United States Patent
Dinh et al.

(10) Patent No.: US 10,953,193 B2
(45) Date of Patent: Mar. 23, 2021

(54) MICROCATHETER WITH MODIFIED PTFE LINER

(71) Applicant: Covidien LP, Mansfield, MA (US)

(72) Inventors: James Q. Dinh, Irvine, CA (US); Jeffrey J. Valko, Irvine, CA (US); Brian M. Strauss, Irvine, CA (US); Adriana X. Peralta, Irvine, CA (US)

(73) Assignee: Covidien LP, Mansfield, MA (US)

( * ) Notice: Subject to any disclaimer, the term of this patent is extended or adjusted under 35 U.S.C. 154(b) by 349 days.

(21) Appl. No.: 13/943,277

(22) Filed: Jul. 16, 2013

(65) Prior Publication Data

US 2015/0025562 A1    Jan. 22, 2015

(51) Int. Cl.
*A61M 25/00* (2006.01)
*A61B 17/12* (2006.01)
*A61F 2/95* (2013.01)

(52) U.S. Cl.
CPC .... *A61M 25/0009* (2013.01); *A61M 25/0045* (2013.01); *A61B 2017/1205* (2013.01); *A61F 2/95* (2013.01); *A61M 25/005* (2013.01); *A61M 2025/0042* (2013.01); *A61M 2025/0047* (2013.01); *A61M 2025/0062* (2013.01)

(58) Field of Classification Search
CPC ............................................ A61M 2025/0047
See application file for complete search history.

(56) References Cited

U.S. PATENT DOCUMENTS

| | | | |
|---|---|---|---|
| 4,671,754 A * | 6/1987 | Okita | B29C 55/005 425/66 |
| 5,121,536 A * | 6/1992 | Pike | A61M 25/0012 29/447 |
| 5,951,539 A | 9/1999 | Nita et al. | |
| 7,435,466 B2 * | 10/2008 | Yoshimoto | A61L 29/041 428/36.9 |
| 9,320,831 B2 | 4/2016 | Trapp | |
| 2002/0022825 A1 | 2/2002 | Saitou et al. | |

(Continued)

FOREIGN PATENT DOCUMENTS

| | | |
|---|---|---|
| EP | 0155337 B1 | 7/1989 |
| EP | 0798010 A1 | 10/1997 |

(Continued)

OTHER PUBLICATIONS

International Search Report and Written Opinion from counterpart International Patent Application No. PCT/US2014/046234, dated Oct. 30, 2014, 7 pp.

(Continued)

*Primary Examiner* — Ryan J. Severson
*Assistant Examiner* — Socrates L Boutsikaris
(74) *Attorney, Agent, or Firm* — Shumaker & Sieffert P.A.

(57) ABSTRACT

In examples, a microcatheter includes an enhanced inner liner that has a low coefficient of friction and improved toughness, which facilitates delivery of expandable vascular reconstruction devices. The microcatheter may include a stretched polytetrafluoroethylene (PTFE) liner, which may be stretched longitudinally and not circumferentially or radially over at least a portion of a length of the microcatheter. The stretched PTFE inner liner may result in the reduction of a delivery friction and improved toughness and resistance to scraping.

27 Claims, 7 Drawing Sheets

(56) References Cited

U.S. PATENT DOCUMENTS

| | | | |
|---|---|---|---|
| 2004/0153049 A1* | 8/2004 | Hewitt et al. | 604/527 |
| 2004/0181208 A1* | 9/2004 | Poole | A61L 29/02 |
| | | | 604/527 |
| 2004/0213936 A1 | 10/2004 | Yoshimoto et al. | |
| 2004/0243102 A1* | 12/2004 | Berg et al. | 604/525 |
| 2006/0206187 A1* | 9/2006 | Parker | A61F 2/95 |
| | | | 623/1.11 |
| 2006/0264898 A1* | 11/2006 | Beasley et al. | 604/506 |
| 2008/0097300 A1 | 4/2008 | Eskaros et al. | |
| 2010/0094392 A1* | 4/2010 | Nguyen | A61F 2/2427 |
| | | | 623/1.11 |
| 2010/0117310 A1 | 5/2010 | Celik et al. | |
| 2010/0160899 A1* | 6/2010 | Gulachenski | A61M 25/0009 |
| | | | 604/525 |
| 2011/0180955 A1 | 7/2011 | Inamoto et al. | |
| 2014/0046138 A1* | 2/2014 | Merk | A61M 25/0012 |
| | | | 600/206 |
| 2014/0081414 A1* | 3/2014 | Hall | A61L 27/16 |
| | | | 623/23.7 |

FOREIGN PATENT DOCUMENTS

| | | |
|---|---|---|
| EP | 1068876 | 1/2001 |
| EP | 1949920 A1 | 7/2008 |
| JP | H06105798 A | 4/1994 |
| JP | H11290448 A | 10/1999 |
| JP | 2000500366 A | 1/2000 |
| JP | 2004340364 A | 12/2004 |
| JP | 2008539025 A | 11/2008 |
| JP | 2010500112 A | 1/2010 |
| JP | 2010536430 A | 12/2010 |
| JP | 2011512183 A | 4/2011 |
| JP | 2012183365 A | 9/2012 |
| WO | 199006150 A1 | 6/1990 |
| WO | 199505555 A1 | 2/1995 |
| WO | 199717998 A1 | 5/1997 |
| WO | 1997017998 A1 | 5/1997 |
| WO | 1998056448 A1 | 12/1998 |
| WO | 2002083223 A1 | 10/2002 |
| WO | 2004064892 A2 | 8/2004 |
| WO | 2006096314 A2 | 9/2006 |
| WO | 2006116438 A2 | 11/2006 |
| WO | 2009023720 A1 | 2/2009 |
| WO | 2009101397 A1 | 8/2009 |
| WO | 2010068793 A1 | 6/2010 |
| WO | 2012044757 A1 | 4/2012 |

OTHER PUBLICATIONS

International Preliminary Report on Patentability from International Application No. PCT/US2014/046234, dated Jan. 28, 2016, 6 pp.
Stenqvist et al., "Stiffness of Central Venous Catheters," Acta Anaesthesiologica Scand., publication Oct. 22, 1983, vol. 27(2) pp. 153-157.
Examination Report No. 2 from counterpart Australian Application No. 2014290621, dated Apr. 3, 2017, 7 pp.
Examination Report from counterpart Canadian Application No. 2,918,490, dated Jan. 25, 2017, 3 pp.
Notice of Reasons for Rejection, and translation thereof, from counterpart Japanese Application No. 2016-526993, dated Dec. 22, 2016, 9pp.
Patent Examination Report from counterpart Australian Application No. 2014290621, dated Oct. 28, 2016, 3 pp.
Examination Report from counterpart Australian Application No. 2014290621, dated Sep. 7, 2017, 4 pp.
Notice of Final Rejection, and translation thereof, from counterpart Japanese Application No. 2016-526993, dated Sep. 4, 2017, 15 pp.
Third Examination Report from counterpart Australian Patent Application No. 2014290621, dated Jul. 12, 2017, 4 pp.
Notice of Acceptance for Patent Application from counterpart Australian Application No. 2014290621, dated Oct. 6, 2017, 8 pp.
Extended European Search Report from counterpart European Application No. 14826551.5, dated Jul. 11, 2016, 4 pp.
"Zeus Catheter Componetry," Zeus, Inc., retrieved on Jun. 8, 2016, accessed from www.zeusinc.com/industries/medical, 1 pp.
Notice of Allowance, from counterpart Japanese Application No. 2016526993, dated Mar. 27, 2018, 3 pp.
First Office Action and Search Report, and translation thereof, from counterpart Chinese Application No. 201480040200.8, dated Jun. 14, 2018, 16 pp.
Notice of Allowance from counterpart Canadian application No. 2,918,490, dated Aug. 3, 2018, 1 pp.
Examination Report from counterpart Canadian Application No. 2,918,490, dated Oct. 31, 2017, 3 pp.
Third Office Action, and partial English translation thereof, from counterpart Chinese Application No. 201480040200.8, dated Jul. 15, 2019, 6 pp.
Second Office Action and Search Report, and translation thereof, from counterpart Chinese Application No. 201480040200.8, dated Feb. 25, 2019, 14 pp.
Extended Search Report from counterpart European Application No. 19159415.9, dated Jun. 19, 2019, 5 pp.
Notice of Intent to Grant and Text Intended to Grant from counterpart European Application No. 14826551.5, dated Oct. 31, 2018, 29 pp.
"PTFE vs. ePTFE," KWO experts in PTFE, retrieved from https://www.kwo-ptfe.de/de/ueber-uns/wissenswertes/ptfe-vs-eptfe on Mar. 10, 2020, 2 pp.
Wilson, "Vascular Access: Principles and Practice", Fifth Edition, 2010, 5 pp. (Applicant points out, in accordance with MPEP 609.04(a), that the year of publication, 2010, is sufficiently earlier than the effective U.S. filing date, so that the particular month of publication is not in issue.).
Ohkura et al., "Fluoroplastics and Fluoroelastomers—Basic Chemistry and High performance Applications," Fluorinated Polymers vol. 2: Applications, Nov. 8, 2016, 9 pp.
"PTFE", Zeus, Inc., http://www.zeusinc.com/extrusionservices/materials/ptfe.aspx, retrieved Dec. 2, 2019, 18 pp.
"Zeus Polymer Extrusions Catalog 11", Zeus, Inc., http://www.zeusinc.com.UserFiles/zeusinc.Documents/Zeus_catalog_revF.pdf, retrieved Dec. 2, 2019, 85 pp.
"Medical", Zeus, Inc., http://www.zeusinc.com/extrusionservices/industries/medical.aspx, retrieved Dec. 2, 2019, 5 pp.
Notice of Opposition, from counterpart European Application No. 14826551.5, dated Dec. 13, 2019, 22 pp.
Communication of Notice of Opposition, from counterpart European Application No. 14826551.5, dated Jan. 2, 2020, 1 pp.
Intention to Grant and Text Intended to Grant from counterpart European Application No. 19159415.9, dated Jun. 12, 2020, 56 pp.

* cited by examiner

MICROCATHETER WITH MODIFIED PTFE LINER

FIELD OF THE INVENTIONS

The devices and methods described below relate to the field of treatments for aneurysms and blood clots.

BACKGROUND OF THE INVENTIONS

Intracranial aneurysms and clots can be treated with implantable devices such as flow diversion tubes, embolization devices, aneurysm bridging devices and scaffolding devices and thrombectomy devices. These devices are delivered through a microcatheter which is first delivered into an intracranial artery affected by an aneurysm or clot. Previously, these devices were preloaded onto the tips of microcatheters for introduction into a patient. More recent devices are not preloaded but are instead loaded via a proximal hub of the microcatheter, after the microcatheter has been placed with its distal tip deep in the intracranial vasculature, near the site of the aneurysm or blood clot. Examples of self-expanding devices delivered through microcatheters include neurovascular remodeling devices such as Covidien's Pipeline® embolization device (which is a braided tube placed to span and bypass an aneurysm) and Covidien's Solitaire® thrombectomy device, which is used to retrieve clots from intracranial arteries, and our own aneurysm bridging device which is used as a scaffold to hold embolic material within an aneurysm. These devices are passed through microcatheters in a compressed state, and released from the microcatheter to expand to a much larger diameter. The compressed shape exerts an outward radial force, which causes friction with the inner wall of the microcatheter and makes delivery difficult. As the devices are forced through the microcatheter, they may scrape the inner wall of the microcatheter and shave off small pieces of the lining, which may then be forced from the microcatheter and deposited in the brain. The FDA's MAUDE Adverse Event Report Database includes reports of liner damage, excess friction, and skiving for various catheters used for delivery of expandable devices.

SUMMARY

The devices and methods described below provide for a easier delivery of expandable vascular reconstruction devices (such as flow diversion tubes, embolization devices, aneurysm bridging devices, scaffolding devices and thrombectomy devices) into the vasculature of a patient, through an improved microcatheter. The improved microcatheter is constructed with a liner that has a low coefficient of friction and increased toughness vis-à-vis typical PTFE or ePTFE liner. The low coefficient of friction reduces the delivery friction between the microcatheter and expandable devices that are passed through the microcatheter, and reduces skiving of liner material that might be deposited into the vasculature.

The microcatheter is enhanced in that the microcatheter includes a stretched PTFE (polytetrafluoroethylene) liner. The PTFE liner (or a portion of the liner) is only stretched longitudinally and not circumferentially or radially over at least a portion of the length of the microcatheter. The enhanced liner results in a reduction of the delivery friction and improved toughness and resistance to scraping. Preferably, the microcatheter comprises a layered construction, including a coil disposed over the liner and a sheath reflowed over the coil. The microcatheter can alternatively include additional layers or it may consist merely of a stretched PTFE liner without additional layers, and the number of layers can vary along the length of the microcatheter.

The microcatheter can be used to deliver aneurysm treatment devices, embolization devices, neurovascular remodeling devices and thrombectomy devices that are loaded via a proximal hub of the microcatheter and then navigated the entire length of the microcatheter before deployment at the desired target site in within the carotid artery.

DETAILED DESCRIPTION OF THE INVENTIONS

Figure 1:
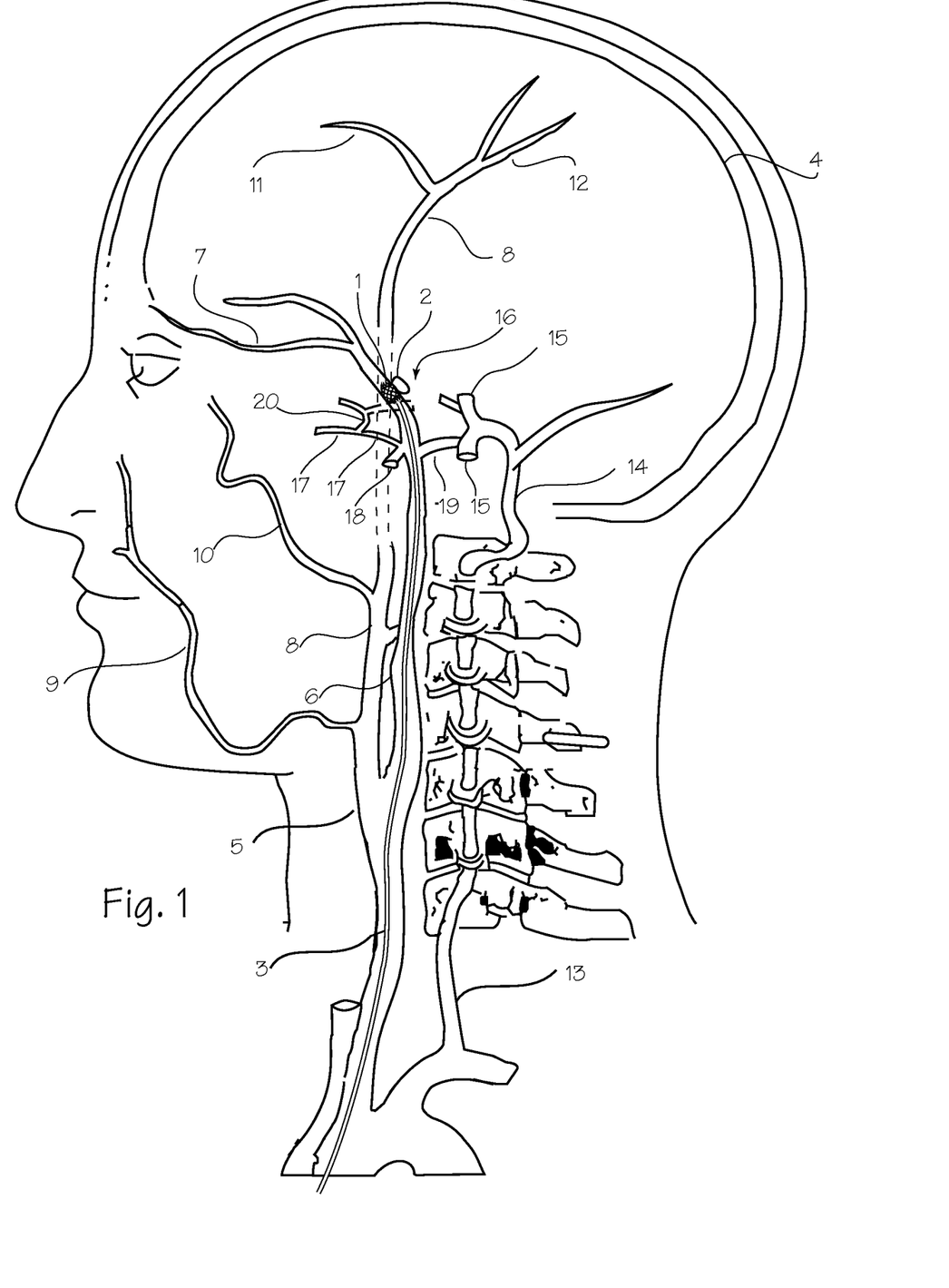
FIG. 1 is a schematic diagram of the vasculature of the brain showing placement of an aneurysm treatment microcatheter with enhanced PTFE liner.

FIG. 1 is a schematic diagram of the vasculature of the brain showing placement of an expandable vascular reconstruction devices 1. The aneurysm treatment device is shown in an exemplary placement within the Circle of Willis. The aneurysm treatment device is delivered to this site of a vascular defect 2 via an enhanced microcatheter 3. The neuro-vasculature, which is the intended environment of use for the aneurysm treatment device, supplies the brain 4 with blood through the carotid and the vertebral arteries on each side of the neck. The important arteries include the carotid artery 5 in the neck and the internal carotid artery 6 which supplies the ophthalmic artery 7. The external carotid 8 supplies the maxillary artery 9, the middle meningeal artery 10, and the superficial temporal arteries 11 (frontal) and 12 (parietal). The vertebral artery 13 supplies the basilar artery 14 and the cerebral arteries including the posterior cerebral artery 15 and the Circle of Willis indicated generally at 16. The siphon of the vertebral artery appears in the intra-cranial vasculature on the vertebral approach to the Circle of Willis. Also supplied by the internal carotid artery are the anterior cerebral artery 17 and the middle cerebral artery 18, as well as the Circle of Willis, including the posterior communicating artery 19 and the anterior communicating artery 20. The siphon of the internal carotid artery 6 appears in the intra-cranial vasculature on the carotid approach into the Circle of Willis. These arteries typically have an internal diameter of about 1 mm to 5 mm, most commonly from 2 to 4 mm. The methods and devices described herein allow access to these arteries and placement of an aneurysm treatment device within these arteries. For example, as shown in FIG. 1, the microcatheter has been used to deliver an expandable vascular reconstruction device 1 to isolate an aneurysm 2 high in the ophthalmic artery, beyond the Circle of Willis.

Figure 2:
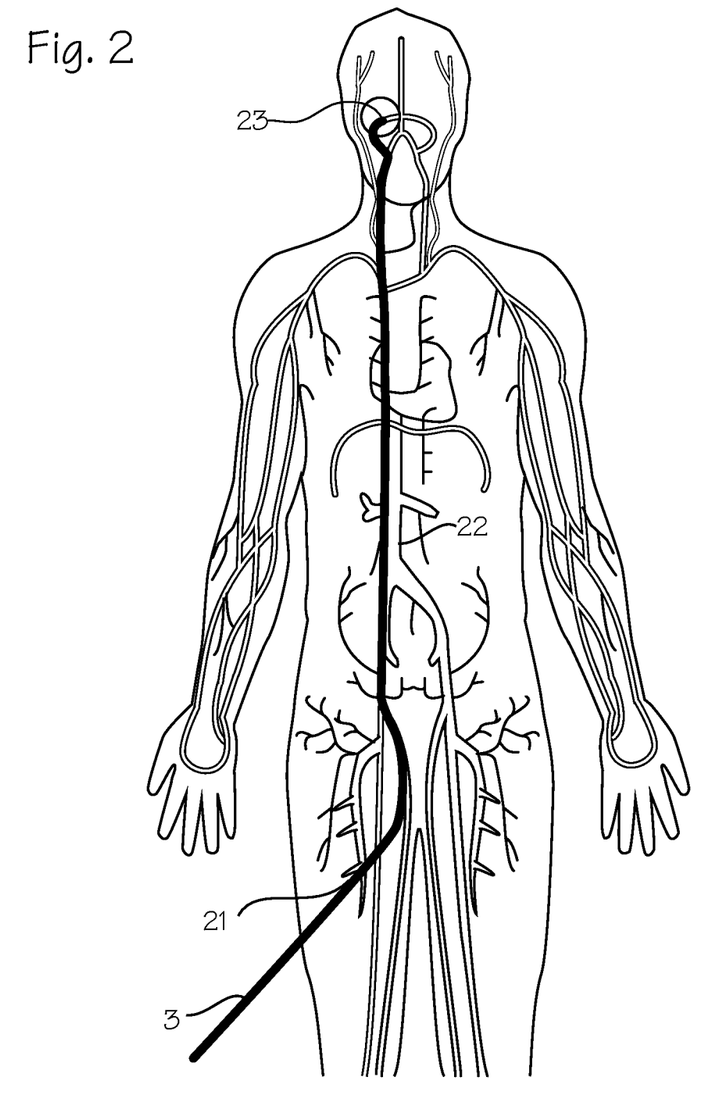
FIG. 2 illustrates the path the microcatheter and treatment device are advanced through a patient.

FIG. 2 illustrates the path through which the microcatheter is advanced through a patient. The microcatheter 3 is introduced through the femoral artery 21, and navigated through the aorta 22 and advanced into the intracranial vascular system of the patient 23. The ultimate target site may be in the carotid arteries, basilar artery, or within or beyond the Circle of Willis or elsewhere in the cerebral vasculature. To deliver the expandable vascular reconstruction devices, the device is fixed to a delivery wire, inserted into the proximal end of the microcatheter 3, and pushed through the entire length of the microcatheter. Within the cerebral vasculature, beyond the proximal portions of the common carotid arteries, the microcatheter is threaded through sharp twists and turns. The expandable vascular reconstruction device is pushed through these sharp twists and turns, and encounters significant friction and resistance from the inner wall of the microcatheter. The microcatheter construction described below reduces this friction and resistance.

Figure 3:
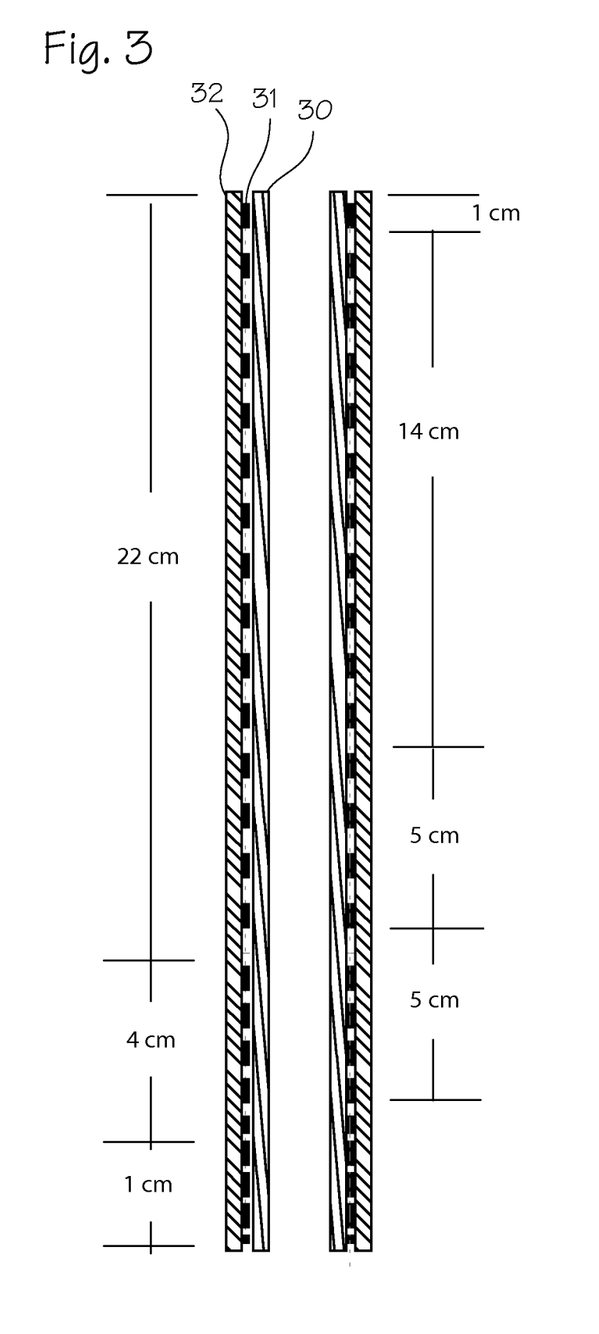
FIGS. 3, 4 and 5 illustrate the enhanced microcatheter.
Figure 4:
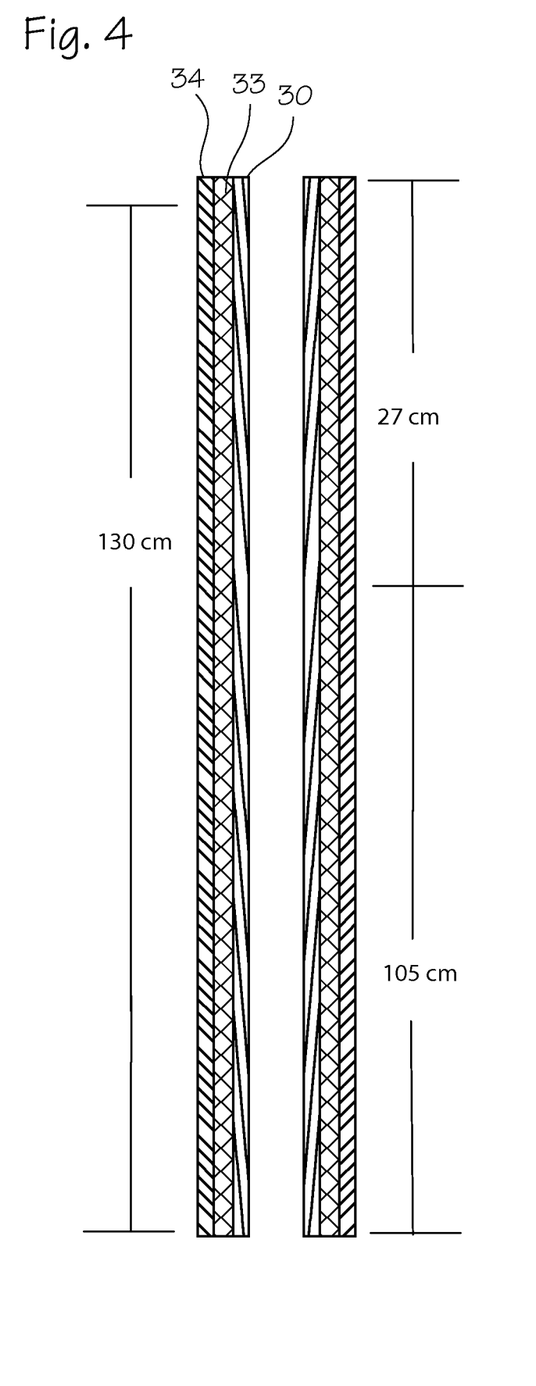
Figure 5:
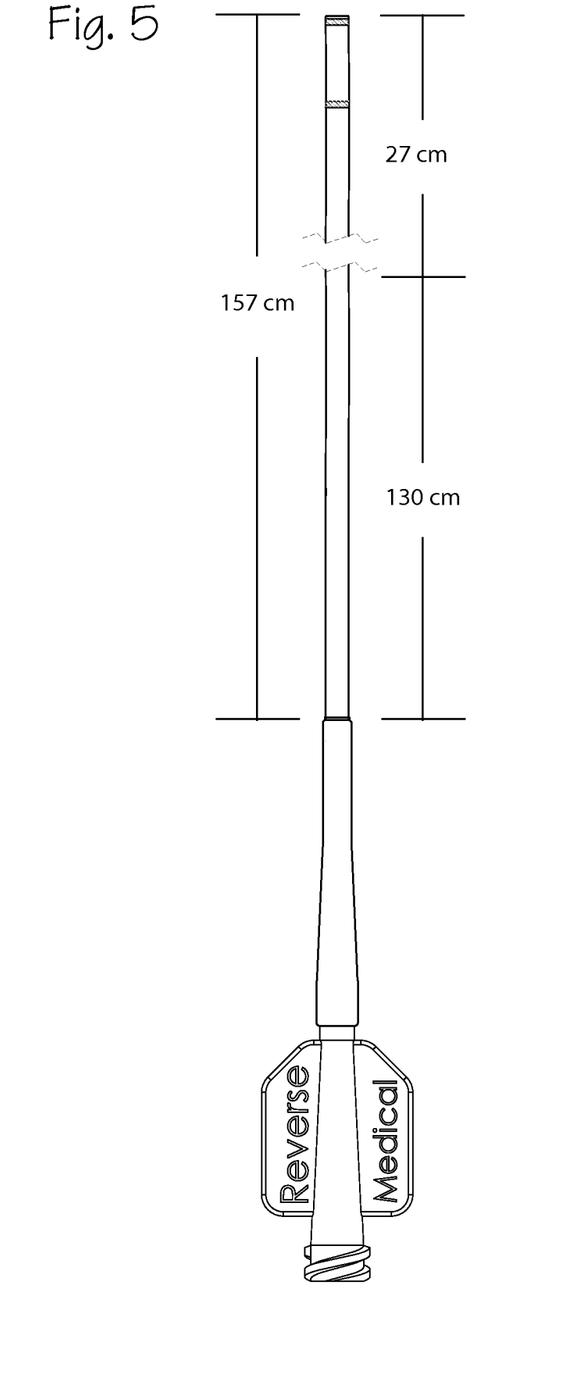

FIGS. 3, 4 and 5 illustrate the microcatheter. The distal segment of the microcatheter is illustrated in FIG. 3. The microcatheter is comprised of three layers. The inner-most layer of the microcatheter includes a stretched PTFE liner or tube 30. The PTFE liner is stretched longitudinally, without being stretched radially or circumferentially. The second layer comprises a coil 31 disposed over at least a portion of the stretched PTFE liner or tube. The third or outermost layer comprises a sheath 32 disposed over the coil. Suitable PTFE materials include PTFE sold under the brand name Zeus® and specifically includes Zeus Sub-Lite-Wall® PTFE tubing, and may include expanded PTFE and heat shrink formulations of PTFE. The coil is preferable nitinol, or any other suitable pseudo-elastic coil. The coil single-wound around the stretched PTFE liner. The single helical coil is preferably wound with a gap ranging between 0.0254 mm to 0.1524 mm between adjacent turns of the coil. Specifically, the distal-most 22 cm are coiled with a 0.1524 mm gap. The 4 cm adjacent to the distal-most 22 cm are wound with a 0.1016 mm gap. The 1 cm adjacent to the previously described 4 cm section is wound with a 0.0254 mm gap. All of these dimensions are approximate, and pertain to a preferred embodiment, and may be varied to obtain more or less flexibility, torqueability and pushability for the distal segment. The outermost layer is formed with various types of pebax (polyether block amide or PEBA) loaded over the nitinol coil. In the distal segment, the distal-most 1 cm is covered with pebax with a hardness of 25D. The 14 cm adjacent to the distal-most 1 cm is covered with pebax with a hardness of 35D. The 5 cm adjacent to the previously described 14 cm is covered with pebax with a hardness of 40D. The next 5 cm adjacent to the previously described 5 cm is covered with pebax with a hardness of 55D. The next 27 cm adjacent to the previously described 5 cm (which spans the distal and proximal segments of the catheter) is covered with pebax with a hardness of 72D. All of these hardness specification are approximate, and pertain to a preferred embodiment, and may be varied to obtain more or less flexibility, torgueability and pushability for the distal segment.

The layers of the proximal segment of the microcatheter are illustrated in FIG. 4. This proximal portion of the microcatheter is also comprised of three layers, which may be continuations of the corresponding layers of the distal segment. The inner-most layer comprises the stretched PTFE liner 30 (that is, a continuation of the PTFE liner of the distal segment). The second layer comprises a pair of cross-wound nitinol coils 33 disposed over the proximal 130 cm of the stretched PTFE liner. The cross-wound coils are preferably wound with a 0.254 mm gap. The third or outermost layer comprises a sheath 34 or tube disposed over the cross-wound nitinol coils. (Other pseudoelastic or resilient materials may be used for the cross wound coils, or a braid of nitinol or other pseudoelastic or resilient materials may be used in place of the cross-wound coils). The outer-most layer is formed with various nylon and pebax materials loaded over the cross-wound nitinol coils. Specifically, 72D pebax is disposed over 27 cm located adjacent (just proximal) to the previously described 12 cm of 40D pebax of the distal segment shown in FIG. 3. Also, nylon (Grilamid L25) is disposed over the 105 cm segment located adjacent to the previously described 27 cm of 72D pebax.

FIG. 5 illustrates the outer layer of the microcatheter, which is coated and contains a hub at the proximal end of the microcatheter. A Luer fitting in the microcatheter hub is used for attachment of accessories. The entire length of the microcatheter is approximately 157 cm, including the distal segment (27 cm long in this example) and the proximal segment (130 cm long in this example).

To form the microcatheter, the PTFE liner is heated and stretched longitudinally, but is not stretched circumferentially or radially. A distal segment of the liner is then wound with a single layer of nitinol coil of varying gaps (as shows in FIG. 3) and the remaining proximal portion of the liner is wound with a pair of cross-wound nitinol coils to form a second layer of the microcatheter (as shown in FIG. 4). Various types of pebax and nylon are then slipped over the second layer of the microcatheter. A layer of heat shrink tube is slipped over the pebax material and is heated segment by segment to shrink and re-flow the pebax. The heat shrink tube is then removed.

Though many methods may be used to stretch the PTFE liner and assemble the microcatheter, the following method may be used. To stretch the PTFE liner longitudinally, while avoiding circumferential or radial stretching, a PTFE tube of appropriate internal diameter, outer diameter and length is pulled and heated to stretch the tube and draw the inner diameter down on a wire with a diameter corresponding to the desired internal diameter of the liner. Thus, a nitinol wire (covered with a PTFE tube, referred to as a beading), is threaded through a PTFE tube, and the wire and tube together are held vertically, suspended from a clamp, and weights are secured to the PTFE tube to apply tension to the tube, and the PTFE tube is heated. The tube is heated and tensioned until stretched 25 to 100%, so that its stretched length is 25 to 100 percent longer than its original length (the inner wall diameter is also drawn down to about 25 to 50% of its original wall thickness). For example, for a PTFE liner of 0.021" (0.53 mm) inner diameter, a 0.00075" (0.02 mm) wall thickness, and 70 inch (178 cm) in length, a PTFE tube of 0.027" (0.69 mm) inner diameter, 0.001-0.0015" (0.0254-0.0381 mm) wall thickness, and initial length of 52 inch (132 cm) can be suspended from a clamp at one end, and weights totally about 115 grams may be secured at the other end, and the PTFE tube can be heated with a heat gun to achieve the PTFE liner of 0.021" diameter and stretched length of 70 inch (178 cm), with a inner wall diameter drawn down to 0.00075" (0.02 mm). Thus, the PTFE tube in this example is stretched in the longitudinal dimension by about 40%. The inner diameter of the tube is drawn down, in this example, from 0.027" to 0.021" (or decreased by about 20-25% of its initial diameter) as well, in response to the longitudinal stretching, but this draw-down, while beneficial in this embodiment, need not be achieved to obtain the benefits of the stretched liner. The heat gun in this example is used to soften the PTFE tube. The heat gun can be drawn over the PTFE tube at constant speed, or it may be drawn over the PTFE tube at different speeds over different longitudinal regions, to create different degrees of stretching, for example to stretch a distal region more than a proximal region (this will result in a more flexible distal region with a thinner wall). Proximal and distal segments of the PTFE heat shrink tube can also be heated differentially in any suitable manner. The PTFE tube may be heated by oven or other techniques. After the PTFE tube is drawn down to the wire, the coil covering the distal segment may be wound over the distal segment, and cross-wound coils covering the proximal segment may be wound over the proximal segment (the proximal cross-wound coils and the distal coil are then welded together at their junction). The outer sheath is applied by slipping pebax tubes and Nylon tubes of appropriate composition and hardness over the distal coil and proximal cross-wound coils, and covering this outer sheath tubing with heat shrink tubing, and heating this assembly to re-flow the pebax and Nylon tubing and compress it into the distal coil and proximal cross-wound coils. The heat shrink tubing used to compress and re-flow the outer sheath material is removed from the three layer microcatheter body and discarded, and the nitinol wire is removed from the stretched PTFE liner, and the three-layer microcatheter body is trimmed (at the distal and proximal ends, as necessary) and secured to a proximal hub or Luer fitting. Radiopaque markers can be applied over the outer sheath, or embedded or sandwiched between layers of the microcatheter, to enhance visualization of the catheter when viewed fluoroscopically during use within the body.

In use, a guide catheter is introduced into the femoral artery via a small incision in the groin of a patient. The guide catheter is navigated from the femoral artery 21 through the aorta 22 and advanced into the carotid artery 23. The ultimate target site may be deep within the intracranial vasculature, perhaps within the Circle of Willis 16 or even deeper. The enhanced microcatheter is introduced through a guide catheter and delivered to the target location in the intracranial vasculature. The expandable vascular reconstruction device is then pushed through the microcatheter to the target site within the intracranial vasculature.

The microcatheter has been described above as a three-layer construction. The microcatheter can consist of the three layers, without additional layers, and this configuration greatly facilitates device delivery because the liner is more lubricious vis-à-vis an un-stretched PTFE tube. Also, the advantage of the stretched liner can be achieved in a microcatheter that includes only the enhanced liner. Specifically, a microcatheter, or a distal segment of the microcatheter, that consist of only the stretched PTFE liner as disclosed above, without additional layers disposed over the PTFE liner. The stretched liner can span the entire length of the microcatheter or may be stretched only on a portion of the microcatheter, such as the distal segment where resistance to passage of the device is greatest.

Figure 6:
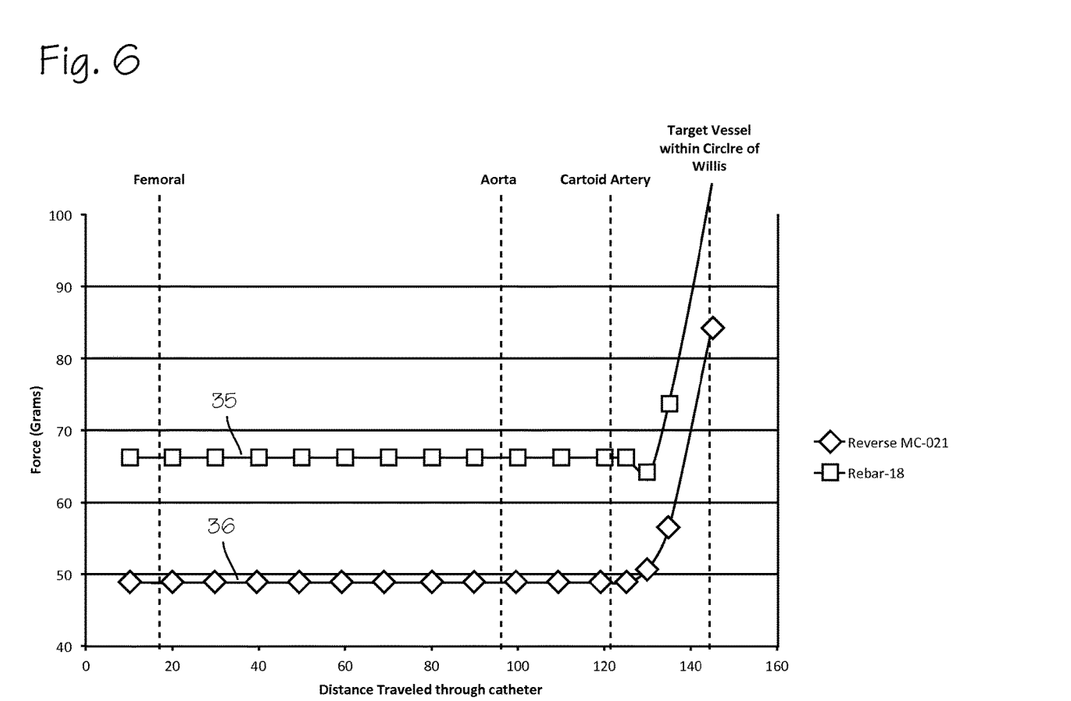
FIGS. 6 and 7 illustrate comparative relationships of displacement to friction between delivery catheters and the microcatheter of FIGS. 3, 4 and 5.

FIG. 6 illustrates the relationship of displacement (distance traveled through the microcatheter) to force (grams) required to push a Covedien Solitaire® mechanical thrombectomy device through a Covidien Rebar® microcatheter as compared to a microcatheter with stretched PTFE liner as described above. The force required to push the device from the point of introduction in the femoral artery through the portion of a Rebar® microcatheter spanning the aorta remains almost constant, at just under 70 grams, as shown by graph line 35. However, the force required to push the device through the final 20 to 30 cm of the microcatheter, which is recognized as the high tortuosity zone, increases greatly. This high tortuosity zone includes the zone where the devices are advanced from the carotid artery to within the Circle of Willis. The graph line 36 depicts the force required to push the same Covedien Solitaire® mechanical thrombectomy device through a microcatheter as described above. The force required to push the device from the introduction point in the femoral artery through the portion of microcatheter spanning the aorta is constant, but less than 50 grams, which is much reduced compared force required for transit of the Rebar® microcatheter. The force required to transit the final 20 to 30 cm of the enhanced microcatheter, in the high tortuosity zone beyond the carotid artery, is significantly lower than that required to transit the corresponding zone within the Rebar microcatheter. As shown in the comparison, the enhanced liner of the microcatheter results in a 15% to 30% decrease in delivery friction when compared to the Covidien Rebar® microcatheter. This facilitates delivery, and reduces the risk of skiving of the liner material by the passing device.

The devices above typically exert an outwardly directed radial force in excess of 0.075 Newtons per millimeter of length. The liner, and especially the inner surface of the liner, is modified to reduce friction between the liner and the device which is pushed through the catheter, such that the longitudinally directed force required to push the device through the microcatheter is less than 380 grams while distal region of the catheter is located within the Circle of Willis.

Figure 7:
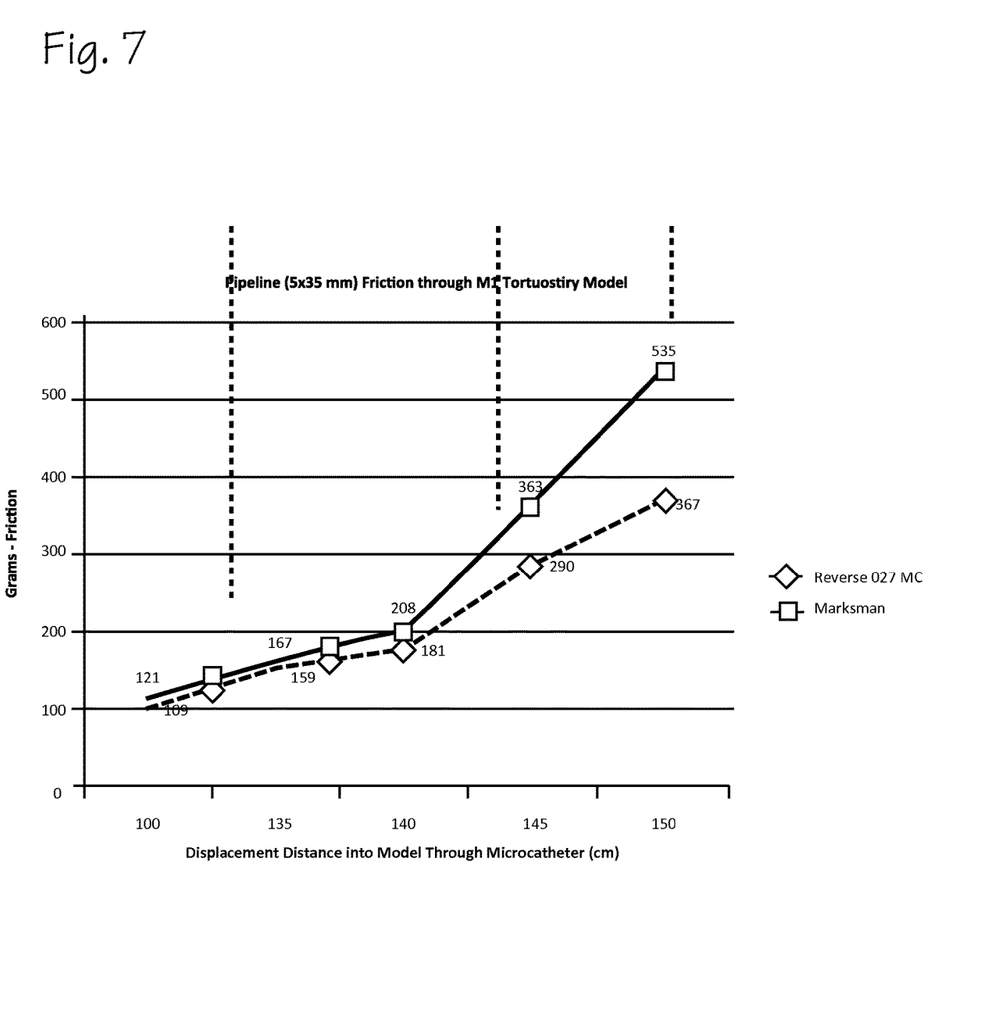

FIG. 7 illustrates the relationship of displacement (distance traveled through the microcatheter) to force (grams) required to push a Covidien Pipeline® embolization device (for aneurysm treatment) through a Covidien Marksman™ microcatheter as compared to a microcatheter with stretched PTFE liner as described above. This graph shows the force required for transit over the last 40-50 cm of the microcatheters. The force required to push the Pipeline® device through the Marksman™ microcatheter is depicted in graph line 37, while the force required to push the Pipeline® device through the enhanced microcatheter is depicted in graph line 38. The enhanced microcatheter, again, presents significantly less resistance to passage of the Pipeline® device than the Marksman™ microcatheter in the tortuous region (the distal 40 or 50 cm of the catheter, which in use reside in the tortuous deep regions of the cerebral vasculature).

Overall, compared to an un-stretched liner, the stretched liner results in a microcatheter with a 40% reduction in friction and the force required to push devices through tortuous regions of the microcatheter, and a 20% reduction of the radial coefficient of friction of the internal surface of the tube. The coefficient of friction as used here refers to a coefficient defined by a test unique to expandable vascular reconstruction devices and microcatheters. This test entails determining the outward radial force (in Newtons) of the expandable vascular reconstruction devices when compressed to match the inner diameter of the microcatheter, and measuring the force (in Newtons) required to pull the expandable vascular reconstruction devices through the microcatheter (while in contact with the liner). The radial coefficient of friction is defined here as the ratio of the radial force exerted by the device to the force required to pull the device through the microcatheter. Under this test, the radial coefficient of friction measured between the expandable vascular reconstruction device and the inner surface of the PTFE liner is in the range of about 0.07 to 0.25. We refer to this coefficient of friction as a "radial" coefficient of friction to distinguish it from the coefficient of friction for PTFE obtained under ASTM D1894, which for PTFE is typically 0.02 to 0.1.

The modified liner is also stronger and tougher than initial PTFE tube. The PTFE liner obtained through the process of stretching described above has a Young's modulus of over 100 Kpsi, typically about 117 Kpsi, which is much higher than the typical Young's modulus (71 Kpsi) of the stock PTFE tubing. The PTFE liner also has greatly increased tensile strength, increased 50 to 100%, from the unmodified PTFE tube, with a tensile strength improved from about 18 kpsi to over 20 kpsi, typically about 28 kpsi.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of making a catheter, the catheter comprising a PTFE liner forming an innermost layer of the catheter, a distal coil disposed over the PTFE liner in a distal region of the catheter, a proximal coil disposed over the PTFE liner in a proximal region of the catheter, and a sheath disposed over the distal coil and the proximal coil, the method comprising:
   longitudinally stretching a portion of a PTFE tube having an initial length and an initial wall thickness to a longer length that is 25% to 100% of the initial length of the portion and a smaller wall thickness that is decreased to 25% to 50% of the initial wall thickness to create the PTFE liner, wherein the PTFE liner is characterized by a Young's modulus greater than 100 kilopound per square inch (kpsi);
   wrapping the distal coil over a distal segment of the PTFE liner; and
   disposing the sheath over the distal coil.

2. The method of claim 1, wherein longitudinally stretching the portion of the PTFE tube to create the PTFE liner comprises:
   tensioning the PTFE tube to lengthen at least the portion of the PTFE tube by 25% to 100% of the initial length of the portion.

3. The method of claim 2, wherein the PTFE tube is characterized by an initial internal diameter, and wherein longitudinally stretching the portion of the PTFE tube to create the PTFE liner comprises:
   drawing down the initial internal diameter of the PTFE tube by about 20% to 25% of the initial internal diameter.

4. The method of claim 1, wherein longitudinally stretching the portion of the PTFE tube to create the PTFE liner comprises:
   tensioning the PTFE tube while heating the PTFE tube, to lengthen at least the portion of the PTFE tube by 25% to 100% of the initial length of the portion.

5. The method of claim 4, wherein the PTFE tube is characterized by an initial internal diameter, and wherein longitudinally stretching the portion of the PTFE tube to create the PTFE liner comprises:
   drawing down the initial internal diameter of the PTFE tube by about 20% to 25% of the initial internal diameter.

6. The method of claim 1, wherein longitudinally stretching the portion of the PTFE tube to create the PTFE liner comprises:
   heating the PTFE tube while tensioning the PTFE tube to lengthen at least the portion of the PTFE tube.

7. The method of claim 1, wherein longitudinally stretching the portion of the PTFE tube to create the PTFE liner comprises:
   tensioning the PTFE tube by suspending the PTFE tube vertically, attaching weights to the PTFE tube, and heating the PTFE tube to lengthen at least the portion of the PTFE tube.

8. The method of claim 1, further comprising:
   wrapping the proximal coil over a proximal segment of the PTFE liner.

9. The method of claim 1, further comprising:
   disposing the proximal coil over a proximal segment of the PTFE liner.

10. A catheter including a 25% to 100% longitudinally-stretched PTFE liner, the PTFE liner having a wall thickness decreased to about 25% to 50% of an initial wall thickness of the PTFE liner prior to being longitudinally-stretched, wherein the longitudinally-stretched PTFE liner is characterized by a Young's modulus greater than 100 kilopound per square inch (kpsi).

11. The catheter of claim 10, where the longitudinally-stretched PTFE liner has a Young's modulus of about 117 kpsi.

12. The catheter of claim 10, wherein the longitudinally-stretched PTFE liner has a tensile strength greater than 20 kpsi.

13. The catheter of claim 10, wherein the longitudinally-stretched PTFE liner has a tensile strength of about 28 kpsi.

14. The catheter of claim 10, wherein the longitudinally-stretched PTFE liner has a radial coefficient of friction of about 0.07 to about 0.25.

15. The catheter of claim 14, further comprising an expandable device positioned within the longitudinally-stretched PTFE liner, wherein the expandable device exerts a radial force on the longitudinally-stretched PTFE liner, and wherein the radial coefficient of friction is a ratio of the radial force exerted by the expandable device to a force required to pull the expandable device through the longitudinally-stretched PTFE liner.

16. The catheter of claim 10, further comprising:
   a coil; and
   a sheath, wherein the coil is positioned between the longitudinally-stretched PTFE liner and the sheath.

17. The catheter of claim 10, wherein a portion of the catheter has only the longitudinally-stretched PTFE liner.

18. The catheter of claim 17, wherein the portion of the catheter is a distal portion.

19. The catheter of claim 10, wherein the longitudinally-stretched PTFE liner spans an entire length of the catheter.

20. The catheter of claim 10, wherein the longitudinally-stretched PTFE liner spans only a portion of a length of the catheter.

21. A catheter including a 25% to 100% longitudinally-stretched PTFE liner, wherein the longitudinally-stretched PTFE liner is characterized by a tensile strength greater than 20 kilopound per square inch (kpsi), wherein the catheter is configured to deploy an expandable device, and wherein an internal surface of the longitudinally-stretched PTFE liner has a radial coefficient of friction of about 0.07 to about 0.25 with respect to the expandable device, the radial coefficient of friction being a ratio of a radial force exerted by the expandable device on the longitudinally-stretched PTFE liner to a force required to pull the expandable device through the longitudinally-stretched PTFE liner when the expandable device is positioned within the catheter.

22. The catheter of claim 21, wherein the longitudinally-stretched PTFE liner has a tensile strength of about 28 kpsi.

23. The catheter of claim 21, further comprising:
a coil; and
a sheath, wherein the coil is positioned between the longitudinally-stretched PTFE liner and the sheath.

24. The catheter of claim 21, wherein a portion of the catheter has only the longitudinally-stretched PTFE liner.

25. The catheter of claim 21, wherein the longitudinally-stretched PTFE liner spans an entire length of the catheter.

26. The catheter of claim 21, wherein the longitudinally-stretched PTFE liner spans only a portion of a length of the catheter.

27. The catheter of claim 21, further comprising the expandable device positioned within the longitudinally-stretched PTFE liner, wherein the expandable device exerts the radial force on the longitudinally-stretched PTFE liner.

* * * * *